United States Patent [19]
Kuo

[11] Patent Number: 5,919,992
[45] Date of Patent: Jul. 6, 1999

[54] SYNTHESIS OF HALOALKYNOL

[75] Inventor: David L. Kuo, Basel, Switzerland

[73] Assignee: Lonza, Inc., Fair Lawn, N.J.

[21] Appl. No.: 08/661,671

[22] Filed: Jun. 11, 1996

[51] Int. Cl.[6] .................................................. C07C 33/42
[52] U.S. Cl. ............................................................. 568/849
[58] Field of Search .................................... 568/873, 849, 568/841

[56] References Cited

U.S. PATENT DOCUMENTS

| | | |
|---|---|---|
| 3,923,870 | 12/1975 | Singer . |
| 4,259,350 | 3/1981 | Morisawa et al. . |
| 4,487,781 | 12/1984 | Morisawa et al. . |
| 4,563,472 | 1/1986 | Inouye et al. . |
| 4,592,773 | 6/1986 | Tamaka et al. . |
| 4,639,541 | 1/1987 | Staiger et al. . |
| 4,731,466 | 3/1988 | Staiger et al. . |
| 4,841,088 | 6/1989 | Kusaba et al. . |
| 4,945,109 | 7/1990 | Rayudu . |
| 5,209,930 | 5/1993 | Bowers-Daines et al. . |
| 5,252,745 | 10/1993 | Bowers-Daines et al. . |
| 5,354,862 | 10/1994 | Hsu . |
| 5,385,902 | 1/1995 | Hsu . |

OTHER PUBLICATIONS

"Total Synthese of Carbohydrates. I. Dihydroxyacetone and DL–Erythrulose", Bull. Chem. Soc. of Japan, 45, 2611–2615 (1972).

Voskresenskii et al., 3–Halopropargyl Alcohols, Uch. Zap., Mosk. Gos. Pedagog. Inst, 38–46, 1971.

Aldrich, Catalog Handbook of Fine Chemicals, pp. 218 and 484, 1996–'97.

*Primary Examiner*—Michael L. Shippen
*Attorney, Agent, or Firm*—Darby & Darby

[57] ABSTRACT

The present invention relates to process of halogenating an alkynol having 3 to 20 carbon atoms to produce a compound having the formula: $R-C\equiv(C-CH_2)_x-OH$, wherein R is F, Cl, Br or I and x is 1 to 18. In particular, this invention provides a process for preparing a halopropynyl alcohol, specifically iodopropynyl alcohol. In one embodiment, iodopropynyl alcohol is produced by sequentially adding potassium hydroxide, potassium iodide and an oxidizing agent to a solution of propynyl alcohol at a rate and temperature sufficient to produce an iodopropynyl alcohol.

13 Claims, No Drawings

SYNTHESIS OF HALOALKYNOL

FIELD OF THE INVENTION

The present invention relates to a process for halogenating an alkynol having 3 to 20 carbon atoms. Specifically, the present invention describes a process for producing iodopropynyl alcohol.

BACKGROUND OF THE INVENTION

Halogenated alkynols are used in a variety of applications. The most widely known and used is iodopropynyl alcohol. Iodopropynyl alcohol, also known as iodopropargyl alcohol and 3-iodo-2-propyn-1-ol, has been used in the production of a wide variety of anti-microbial and anti-fugal agents. The use of iodopropynyl alcohol in the production of these compounds is described in the prior art, for example, in U.S. Pat. No. 4,945,109 to Buckman Laboratories International Inc., U.S. Pat. No. 4,639,541 to Consortium Fur Elektrochemische Industrie GmBH DE, U.S. Pat. No. 4,563,472 to Meiji Seika Kaisha, Ltd., U.S. Pat. Nos 5,209,930; 5,252,745; 5,354,862 and 5,385,902 to Rohm and Haas, U.S. Pat. No. 4,841,088 to Sumitomo, U.S. Pat. No. 4,731,466 to the Dow Chemical Co., U.S. Pat. No. 4,487,781 and 4,259,350 to Sankyo Co. and U.S. Pat. No. 4,592,773 to Mitsui Toatsu Chemicals.

The process for producing iodopropynyl alcohol described in the literature involves treating propynyl alcohol with iodine and potassium hydroxide in methanol. The crude product obtained is impure and must be recrystallized or distilled. Recrystallizing iodopropynyl alcohol is cumbersome due to the vesicant nature of the compound. The percent yield and purity of iodopropynyl alcohol produced by methods described in the prior art are extremely low, usually around 50%. Furthermore, it is extremely expensive to produce iodopropynyl alcohol using conventional methods and a number of environmentally hazardous wastes are produced. Thus, a method of producing halopropynyl alcohol, and in particular iodopropynyl alcohol, with a high yield and purity which is cost-effective and does not produce a significant number of environmentally hazardous waste products is currently not available.

SUMMARY OF THE INVENTION

The present invention provides a process of producing haloalkynols having 3 to 20 carbon atoms. Haloalkynols are produced in this invention by reacting the alkynol with a base, an alkali metal halide or iodine and an oxidizing agent. In particular, the invention relates to a process of iodinating propynyl alcohol to produce iodopropynyl alcohol by reacting propynyl alcohol with potassium hydroxide, potassium iodide and an oxidizing agent.

In contrast to the haloalkynols obtained by the process heretofore used, the process of this invention is cost-efficient and produces compounds with a high yield and purity. The yield and purity range from approximately 80% to greater than or equal to 95%. Furthermore, compounds produced by the reaction of this invention do not require an additional purification step.

DETAILED DESCRIPTION OF THE INVENTION

The essential components, their relevant proportions, and the reaction conditions of the invention are set forth below. Unless otherwise indicated, all percentages are on a molar weight basis. All patents, publications and test methods mentioned herein are incorporated by reference.

The present invention relates to a process of halogenating an alkynol having 3 to 20 carbon atoms to produce a compound having the general formula (I): $R-C\equiv C-(CH_2)_x-OH$, wherein R is I and x is 1 to 18. As used in the present invention, the term "halogenating" denotes adding a halogen to the acetylenic terminal end of an alkynol. Examples of halogens which may be added by this process include fluorine, chlorine, bromine and iodine. One embodiment of the invention relates to a process of halogenating propynyl alcohol to produce a compound having the general formula (II): $R-C\equiv C-CH_2-OH$, wherein R is I. In a preferred embodiment of the invention, iodine is added to the acetylenic terminal end of the propynyl alcohol to produce iodopropynyl alcohol having the formula (III): $I-C\equiv C-CH_2-OH$.

To produce a haloalkynol having 3 to 20 carbon atoms according to this invention, the alkynol is reacted with a base, an alkali metal halide or iodine and an oxidizing agent. One embodiment of this invention is a process for producing iodopropynyl alcohol by reacting propynyl alcohol with potassium hydroxide, potassium iodide and an oxidizing agent. The particular temperature and pressure in the reaction and the molar ratio of each compound to the alkynol in the reaction mixture is outlined below. Generally, the process of this invention is run at a temperature ranging from −10° C. to 30° C. In one preferred embodiment, the process is run at a temperature ranging from 2° C. to 7° C.

In the reaction of this invention, an alkynol having 3 to 20 carbon atoms such as propynyl alcohol may be initially mixed with a solvent. Solvents used in the process of this invention include, for example, methyl tert-butyl ether, methanol, ethanol, propanol, isopropanol, butanol and water. The alkynol solution produced may be cooled to a temperature less than 10° C., preferably to approximately 2° C. The concentration of the alkynol in the solvent may range from approximately 0.1 molar to 10 molar, preferably 2.4 molar to 3.0 molar.

The base used in the reaction may be a metal hydroxide such as, $NaOH$, $KOH$, $Mg(OH)_2$, $Ca(OH)_2$, $LiOH$, or a potassium, or sodium alkoxy salt, such as, $K_2CO_3$, $Na_2CO_3$, $CH_3ONa$, $CH_3CH_2ONa$, $(CH)_3COK$ and $(CH_3)_2CHCH_2ONa$. The molar ratio of base to alkynol may range from approximately 1:1 to 1:20. In one embodiment, potassium hydroxide is used in an amount ranging from 1:1 to 1:20. In a preferred embodiment, the potassium hydroxide to propynyl alcohol molar ratio is approximately 1:2.8.

The base is added to the reaction mixture at a rate sufficient to maintain a reaction temperature of less than 20° C. preferably between approximately 12° C. to approximately 20° C., for example, over a period of approximately 30 to 60 minutes. The temperature is maintained at this temperature to keep the alkynol, such as propynyl alcohol, intact in the reaction mixture before adding the oxidizing agent.

Alkali metal halides which may be used in the reaction include, for example, $LiI$, $KI$, $NH_4I$, and $NaI$. KI is the most preferred. Iodine may also be added rather than an alkali metal halide. The molar ratio of the alkali metal halide or iodine to the alkynol used may be from 1:1 to 1:2. In one preferred embodiment, the ratio of potassium iodide to propynyl alcohol is 1:1.

The alkali metal halide is added to the reaction mixture over a period of approximately 2 to 15 minutes and the reaction temperature is maintained at approximately 2° C. to approximately 7° C., preferably approximately 2° C.

Oxidizing agents which may be used in the reaction of this invention include, for example, dihalodimethylhydantoins (such as, 1,3-dichloro-5,5-dimethylhydantoin (DCDMH), bromochlorodimethylhydantoin (BCDMH) and 1,3-dibromo-5,5- dimethylhydantoin (DBDMH)), sodium dichloro-s-triazinetrione, sodium hypochlorite (NaOCλ), N-bromosuccinimide, N-chlorosuccinimide, chlorine and trichloroisocyanuric acid.

The molar ratio of oxidizing agent to alkynol may range from approximately 1:1 to 1:4. In one preferred embodiment, DCDMH is the oxidizing agent and the molar ratio is 1:2.

The oxidizing agent is added to the reaction mixture at a rate sufficient to maintain the reaction temperature at approximately 2° C. to approximately 11° C., for example, over a period of approximately 15 minutes to 2 hours. This temperature minimizes the formation of side products in the reaction mixture.

In a preferred embodiment, 1.0 mole of propynyl alcohol, 0.35 mole of base, 1.0 mole of potassium halide and 0.5 mole of oxidizing agent are added in the reaction. Reacting 1.0 mole of propynyl alcohol, 0.35 mole of potassium hydroxide, 1.0 mole of potassium iodide and 0.5 mole of DCDMH is the most preferred method for producing iodopropynyl alcohol.

The reaction mixture may be mixed for approximately 30 minutes to 3 hours. The alkynol quantitatively reacted with the other reactants in the reaction mixture. The iodoalkynol is isolated by conventional extraction techniques, for example, by extracting the reaction mixture with methyl tert-butyl ether and drying with a drying agent such as sodium sulfate, removing the drying agent by filtration and removing the solvent under vacuum.

The reaction described by this invention may be run at a pressure ranging from 1 atm to 20 atm. Preferably, the reaction is run at atmospheric pressure.

To further illustrate the present invention, reference is made to the following examples. It should be understood that the invention is not limited to the specific examples or the details described therein. The results obtained from the experiments described in the examples are shown in the accompanying figures and tables.

EXAMPLE 1

Iodination of propynyl alcohol using 1,3-Dichloro-5,5-dimethylhydantoin (DCDMH) in Water Propynyl alcohol (Aldrich, 99%) (113.3 g, 2.00 mol) was dissolved in water (750 ml), and cooled to approximately 3° C. Potassium hydroxide (Aldrich, 85%) (46.2 g, 0.70 mol) was added to the propynyl alcohol solution at a rate so that the temperature of the mixture was less than 20° C. during the reaction. Potassium iodide (VWR, 99%) (335 g, 2.00 mol) was added to the reaction mixture to produce a yellowish clear reaction mixture. DCDMH (Lonza, ~99%) (205 g, 1.00 mol) was added over a period of approximately 2 hours so that the temperature was maintained below 7° C. A pale yellow heterogeneous reaction mixture was stirred for approximately 1.0 hour at approximately 3° C. The lower layer, containing the product, was separated from the upper layer. The upper layer was extracted with methyl tert-butyl ether (EM Science, 99.9%) (3×200 ml). The combined organic layers were added to the lower layer. Any remaining water was separated and the reaction mixture was dried ($Na_2SO_4$). The drying agent was removed by filtration. The solvent was removed under vacuum. Further overnight high vacuum drying gave 326 g (HPLC: 90.2%) of iodopropynyl alcohol as a pale yellowish solid, resulting in a yield of approximately 81.0%.

EXAMPLE 2

Iodination of propynyl alcohol using DCDMH with a molar ratio of 1:4 and KOH with a molar ratio of 1:1 in MeOH This reaction is similar to the reaction of Example 1 except that iodine rather than KI was used and the amount of DCDMH added was reduced.

Propynyl alcohol (Aldrich, 99%) (20 g, 0.36 mol) was dissolved in methanol (VWR, anhydrous) (130 ml). Potassium hydroxide (Aldrich, 85%) (23.6 g, 0.36 mol) was added to the propynyl alcohol solution at a rate so that the temperature of the mixture was less than 20° C. during the reaction. The reaction mixture was cooled to approximately 3° C. as iodine (EM Science 99.8%) (45.3 g, 0.18 mol) was slowly added over a period of approximately 15 minutes. DCDMH (Lonza, ~98%) (17.9 g, 0.09 mol) was added in approximately 15 minutes. The resulting pale yellow heterogeneous mixture was stirred for approximately 3 hours at 3° C. Methanol was removed under reduced pressure and work-up was affected by extracting the reaction mixture with methyl tert-butyl ether (EM Science, 99.9%) (200 ml) and water (200 ml). After extraction with more methyl tert-butyl ether (2×100 ml), the combined organic layers were dried ($Na_2SO_4$). Filtration of the drying agent, followed by the removal of solvent under vacuum and further overnight high vacuum drying gave 60 g (HPLC: 97%) of iodopropynyl alcohol as a pale yellowish solid, resulting in a yield of approximately 90%.

EXAMPLE 3

Iodination of propynyl alcohol using 1,3-Dichloro-5,5-dimethylhydantoin (DCDMH) and KOH with a molar ratio of 1:1 in MeOH This Example is similar to Example 1 except the molar ratio of KOH to propynyl alcohol was 1:1 rather than 1:2.8 and the molar ratio of DCDMH was 1:1 rather than 1:2.

In this reaction, equal molar amounts of each reactant was used. Propynyl alcohol (Aldrich Chemical Co., 99%) (20.2 g, 0.36 mol) was dissolved in methanol (VWR) (250 ml), and cooled to approximately 3° C. Potassium hydroxide (Aldrich, 85%) (23.6 g, 0.36 mol) was added to propynyl alcohol solution at a rate so that the temperature of the mixture was maintained below 12° C. Potassium iodide (VWR, 99%) (59.8 g, 0.36 mol) was added in approximately two minutes to produce a yellowish clear reaction mixture. DCDMH (Lonza, ~99%) (70.9 g, 0.36 mol) was reacted at a rate sufficient to maintain the temperature below 7° C. The pale yellow heterogeneous mixture produced was stirred for approximately 1.5 hours. The temperature of the reaction temperature was approximately 3° C. Methanol was removed under vacuum and work-up was affected by extracting the reaction mixture with methyl tert-butyl ether (EM Science, 99.9%) (3×200 ml), and dried ($Na_2SO_4$). Filtration of the drying agent, followed by the removal of solvent under vacuum and further overnight high vacuum drying gave 61.1 g (HPLC:97.5%) of yellowish oil, resulting in a yield of approximately 91.8%. The oil solidified upon standing in the sample flask as a pale yellow solid.

EXAMPLE 4

Iodination of propynyl alcohol using 1,3-Dichloro-5,5-dimethylhydantoin (DCDMH and KOH with a molar ratio of 1:1 in water Equal molar amounts of each reactant were used in the reaction. The reaction is similar to Example 3 except that the solvent used was water rather than methanol.

Propynyl alcohol (Aldrich, 99%) (20.2 g, 0.36 mol) was dissolved in water (160 ml), and cooled to approximately 3° C. Potassium hydroxide (Aldrich, 85%) (23.6 g, 0.36 mol) was added to the propynyl alcohol solution at a rate so that the temperature of the mixture was less than 15° C. Next, potassium iodide (VWR, 99%) (59.8 g, 0.36 mol) was added to the reaction mixture in approximately 2 minutes, producing a yellowish clear reaction. DCDMH (Lonza, ~99%) (70.9 g, 0.36 mol) was then added over a period of approximately 40 minutes so that the temperature of the reaction was maintained below 11° C. At the completion of the reaction, the resulting pale yellow heterogeneous mixture was stirred for approximately 3.0 hours at approximately 5° C. Work-up was affected by extracting the reaction mixture with ethyl acetate (J. T. Baker, 99.9%) (3×200 ml), and dried ($Na_2SO_4$). Filtration of the drying agent, followed by the removal of solvent under vacuum and further overnight high vacuum drying gave 67.8 g (HPLC:88.3%) of yellowish oil, resulting in a yield of approximately 85%.

This Example and Example 3 show, regardless of whether the solvent is methanol or water, the reaction of this invention results in the production of a halopropynyl alcohol with a significantly higher yield and purity.

EXAMPLE 5

Iodination of propynyl alcohol using 1,3-Dichloro-5,5-dimethylhydantoin (DCDMH) and KOH with a molar ratio of 1:2 in MeOH This Example is similar to Example 3 except that the molar ratio of KOH and DCDMH to propynyl alcohol was 1:2 rather than 1:1.

Propynyl alcohol (Aldrich, 99%) (56.6 g, 1.00 mol) was dissolved in methanol (VWR, anhydrous) (380 ml), and cooled to approximately 3° C. Potassium hydroxide (Aldrich, 85%) (35.1 g, 0.50 mol) was added to the propynyl alcohol solution at a rate so that the temperature of the reaction mixture was less than 12° C. Potassium iodide (VWR, 99%) (166 g, 1.00 mol) was added to the reaction mixture to produce a yellowish clear reaction mixture. DCDMH (Lonza, ~99%) (108 g, 0.55 mol) was next added at a rate so that the temperature of the reaction was maintained below 7° C. DCDMH was added over a period of approximately 90 minutes. At the completion of the DCDMH addition, the resulting pale yellow heterogeneous mixture was stirred for 1.7 hours at approximately 3° C. Methanol was removed under vacuum and work-up was affected by extracting the reaction mixture with methyl tert-butyl ether (EM Science, 99.9%) (3×200 ml), and dried ($Na_2SO_4$). The drying agent was removed by filtration. The solvent was removed under vacuum. Further overnight high vacuum drying gave 177 g (HPLC:$\geq$95.0%) of iodopropynyl alcohol as a yellowish oil, resulting in a yield of approximately 92.1%. The oil solidified upon standing in the sample flask as a pale yellow solid.

This Example illustrates that a 50% reduction in the moles of base (KOH) and oxidizing agent (DCDMH) added to the reaction (See Table 1), does not significantly affect the purity and yield of compound produced. The compound was 95% pure and had a yield of 92.1% (compared to a purity of 97.5% and a yield of 91.8%).

EXAMPLE 6

Iodination of propynyl alcohol using 1,3-Dichloro-5,5-dimethylhydantoin (DCDMH) and KOH with a molar ratio of 1:2 in water This reaction is similar to the reaction of Example 5 except that the solvent used was water rather than methanol.

Propynyl alcohol (Aldrich, 99%) (56.66 g, 1.00 mol) was dissolved in water (380 ml), and cooled to approximately 3° C. Potassium hydroxide (Aldrich, 85%) (29.7 g, 0.45 mol) was added to the propynyl alcohol solution at a rate so that the temperature of the mixture was less than 15° C. during the reaction. Potassium iodide (VWR, 99%) (166 g, 1.00 mol) was added to the reaction mixture to produce a yellowish clear reaction mixture. DCDMH (Lonza, ~99%) (105 g, 0.55 mol) was added over a period of approximately 90 minutes so that the temperature was maintained below 7° C. A pale yellow heterogeneous reaction mixture was stirred for approximately 0.5 hours at approximately 5° C. Work-up was affected by extracting the reaction mixture with methyl tert-butyl ether (EM Science, 99.9%) (3×200 ml), and dried ($Na_2SO_4$). The drying agent was removed by filtration. The solvent was removed under vacuum. Further overnight high vacuum drying gave 162 g (HPLC:$\geq$95%) of iodopropynyl alcohol as a pale yellowish solid, resulting in a yield of approximately 85.0%.

EXAMPLE 7

Iodination of propynyl alcohol using DCDMH with a molar ratio of 1:2 and KOH with a molar ratio of 1:4 in MeOH This reaction is similar to the reaction of Example 5 except that the molar ratio of KOH to propynyl alcohol was 1:4 rather than 1:2.

Propynyl alcohol (Aldrich, 99%) (10 g, 0.18 mol) was dissolved in methanol (VWR, anhydrous) (65 ml), and cooled to approximately 3° C. Potassium hydroxide (Aldrich, 85%) (2.94 g, 0.045 mol) was added to the propynyl alcohol solution. Potassium iodide (VWR, 99%) (30 g, 0.18 mol) was next added to produce a yellowish clear reaction mixture. DCDMH (Lonza, ~99%) (18.3 g, 0.09 mol) was added in approximately 50 minutes, thereby maintaining a reaction temperature below 10° C. The resulting pale yellow heterogeneous mixture was stirred for approximately 1.5 hours at 3° C. Methanol was removed under vacuum and work-up was affected by extracting the reaction mixture with methyl tert-butyl ether (EM Science, 99.9%) (2×100 ml), and dried ($Na_2SO_4$). Filtration of the drying agent, followed by the removal of solvent under vacuum and further overnight high vacuum drying gave 28 g (HPLC:$\geq$95%) of iodopropynyl alcohol as a yellowish oil, resulting in a yield of approximately 82 %.

Though the molar ratio of KOH to alcohol was reduced to 1:4, the purity of iodopropynyl alcohol remained high, i.e., 95%.

EXAMPLE 8

Iodination of propynyl alcohol using sodium hypochlorite in MeOH

This reaction is similar to the reaction of Example 1 except that the oxidizing agent is NaOCλ rather than DCDMH.

Propynyl alcohol (Aldrich, 99%) (10.1 g, 0.18 mol) was dissolved in methanol (VWR, anhydrous) (80 ml) and cooled to approximately 3° C. Potassium hydroxide (Aldrich, 85%) (11.8 g, 0.18 mol) was added to the propynyl alcohol solution at a rate so that the temperature of the mixture was maintained below 15° C. Next, potassium iodide (VWR, 99%) (29.9 g, 0.18 mol) was added in approximately 1 minute to produce a yellowish clear reaction mixture. NaOCλ (Weis, 4.6%) (289 g, 0.18 mol) was added at a rate to maintain a temperature below 10° C., approximately 90 minutes. The resulting pale yellow homogeneous solution was stirred for approximately 2.5 hours at 5° C. Work-up was achieved by removing methanol under vacuum, extracting the reaction mixture with ethyl acetate (J. T. Baker, 99.9%) (3×200 ml) and drying the mixture ($Na_2SO_4$). The drying agent was separated by filtration, followed by the removal of the solvent under vacuum. A further overnight high vacuum drying gave 29.9 g (HPLC:94.3%) of very pale yellowish solid, resulting in a yield of approximately 86.9%.

As illustrated by this example, when the oxidizing agent NaOCλ is used in the reaction, a compound with a high purity and high yield is produced.

EXAMPLE 9

Iodination of propynyl alcohol using sodium hypochlorite in water

This reaction is similar to the reaction of Example 8 except that the solvent is water rather than methanol.

Propynyl alcohol (Aldrich, 99%) (40.4 g, 0.71 mol) was dissolved in water (210 ml), and cooled to approximately 3° C. Potassium hydroxide (Aldrich, 85%) (47 g, 0.71 mol) was added to the propynyl alcohol solution at a rate so that the temperature of the mixture was maintained below 20° C. Next, potassium iodide (VWR, 99%) (120 g, 0.71 mol) was added to produce a yellowish clear reaction mixture. Potassium iodide was added over a period of approximately 5 minutes. NaOCλ (EM Science, 3.3%) (1610 g, 0.71 mol) was then reacted at approximately 6° C. The resulting pale yellow homogeneous solution was stirred for approximately 1.5 hours at approximately 5° C. Work-up was achieved by extracting the reaction mixture with methyl tert-butyl ether (EM Science, 99.9%) (3×200 ml), and drying the mixture ($Na_2SO_4$). The drying agent was removed by filtration. The solvent was removed under vacuum. Further overnight high vacuum drying gave 131 g (HPLC:93.9%) of pale yellowish oil, resulting in a yield of approximately 90%. The oil solidified upon standing in the sample flask as a pale yellow solid.

EXAMPLE 10

Iodination of propynyl alcohol using Bromo-chloro-dimethylhydantoin (BCDMH) with a molar ratio of 1:2 and KOH with a molar ratio of 1:2 in MeOH Propynyl alcohol (Aldrich, 99%) (10 g, 0.18 mol) was dissolved in methanol (VWR, anhydrous) (70 ml), and cooled to approximately 3° C. Potassium hydroxide (Aldrich, 85%) (5.9 g, 0.09 mol) was added to the propynyl alcohol solution at a rate so that the temperature of the reaction mixture was maintained below 12° C. Next, potassium iodide (VWR, 99%) (30 g, 0.18 mol) was added to produce a yellowish clear reaction mixture. BCDMH (Lonza, ~99%) (22 g, 0.09 mol) was added at a rate so that the temperature of the reaction was maintained below 6° C. throughout the addition. The BCDMH was added over a period of approximately 90 minutes. The reaction mixture was stirred for approximately 2.6 hours at a temperature of approximately 3° C. Methanol was removed under vacuum and work-up was affected by extracting the reaction mixture with methyl tert-butyl ether (EM Science, 99.9%) (2×100 ml), and dried ($Na_2SO_4$). The drying agent was removed by filtration. The solvent was removed under vacuum. Further overnight high vacuum drying gave 30 g (HPLC:≧95.0%) of iodopropynyl alcohol as a yellowish oil, resulting in a yield of approximately 89%. The oil solidified upon standing in the sample flask as a pale yellow solid.

As illustrated by this example, when the oxidizing agent BCDMH is used in the reaction, a compound with a high purity and high yield is produced.

TABLE 1

Summary of Examples 1–10**

| | Example | | | | | | | | | |
|---|---|---|---|---|---|---|---|---|---|---|
| | 1 | 2 | 3 | 4 | 5 | 6 | 7 | 8 | 9 | 10 |
| Solvent (W-Water) (M-Methanol) | W | M | M | W | M | W | M | M | W | M |
| 2-Propyn-1-ol | 2.00 | .36 | .36 | .36 | 1.0 | 1.0 | .18 | .18 | .71 | .18 |
| KOH | 0.70 | .36 | .36 | .36 | .50 | .45 | .045 | .18 | .71 | .09 |
| KOH: alcohol | 1:2.8 | 1:1 | 1:1 | 1:1 | 1:2 | 1:2 | 1:4 | 1:1 | 1:1 | 1:2 |
| KI | 2.00 | .18* | .36 | .36 | 1.0 | 1.0 | .18 | .18 | .71 | .18 |
| KI: alcohol | 1:1 | 1:2* | 1:1 | 1:1 | 1:1 | 1:1 | 1:1 | 1:1 | 1:1 | 1:1 |
| OA*** | DC | DC | DC | DC | DC | DC | DC | OCl | OCl | BC |
| OA | 1.0 | .09 | .36 | .36 | .55 | .55 | .09 | .18 | 0.71 | .09 |
| OA: alcohol | 1:2 | 1:4 | 1:1 | 1:1 | 1:2 | 1:2 | 1:2 | 1:1 | 1:1 | 1:2 |
| purity (%) | 90.2 | 97 | 97.5 | 88.3 | ≧95 | ≧95 | ≧95 | 94.3 | 93.9 | ≧95 |
| yield (%) | 81 | 90 | 91.8 | 85 | 92.1 | 85 | 82 | 86.9 | 90 | 89 |

*Iodine rather than KI was used.
**All amounts and reactions are expressed in moles.
***DC = DCDMH
OCl = NaOCl
BC = BCDMH The above tabular summary shows the moles of each reactant in the reactions described in Examples 1–10 and the molar ratio of reactant to propynyl alcohol used in the reactions. The purity and yield of iodopropynyl alcohol produced by each reaction is also shown. These results illustrate the process of this invention results in haloalkynols having high yields and purity over a wide range of reactant concentrations and using various reactants. To further illustrate the improvements provided by this invention, a comparative example provided below describes the conventional method for producing iodopropynyl alcohol.

COMPARATIVE EXAMPLE

Iodination of propynyl alcohol using iodine in MeOH

Propynyl alcohol (Aldrich, 99%) (20.2 g, 0.36 mol) was dissolved in methanol (VWR, anhydrous) (250 ml), and cooled to approximately 3° C. Potassium hydroxide (Aldrich, 85%) (23.6 g, 0.36 mol) was added to the propynyl alcohol solution at a rate so that the temperature of the mixture was less than 12° C. Iodine (EM Science, 99.8%) (91.5 g, 0.36 mol) was then added to the reaction mixture at a rate so that the temperature of the reaction was maintained below 5° C. (approximately 60 minutes). The resulting dark red heterogeneous mixture was stirred for approximately 2 hours. Work-up was affected by extracting the reaction mixture with methyl tert-butyl ether (EM Science, 99.9%) (3×200 ml), and dried ($Na_2SO_4$). Filtration of the drying agent, followed by the removal of solvent under vacuum and further overnight high vacuum drying gave 60.9 g (HPLC:55.4%) of yellowish oil, resulting in a yield of approximately 51.9%.

As illustrated by Example 1 and the Comparative Example, using the process for producing iodopropynyl alcohol described by this invention (Example 1) compared to methods described in the prior art (Comparative Example) results in a significantly higher yield (90.2% compared to 51.9%) and purity (81.0% compared to 55.4%).

What is claimed is:

1. A process for preparing an iodoalkynol having 3 to 20 carbon atoms which comprises sequentially adding:
   (a) a base;
   (b) an alkali metal iodide or iodine; and
   (c) an oxidizing agent which is dichlorodimethylhydantoin, bromochlorodimethylhydantoin, or N-bromosuccinimide, trichloroisocyanuric acid, N-chlorosuccinimide, or dibromodimethylhydantoin; to a solution of an alkynol having 3 to 20 carbon atoms at a rate and temperature sufficient to produce the iodoalkynol, wherein the molar ratio of base to alkynol is from 1:1 to 1:20, the molar ratio of alkali metal iodide to alkynol is from 1:1 to 1:2, and the molar ratio of oxidizing agent to alkynol is from 1:1 to 1:4.

2. The process according to claim 1 wherein the iodoalkynol is iodopropynyl alcohol.

3. The process according to claim 1 wherein the base is a metal hydroxide.

4. The process according to claim 3 wherein the base is KOH.

5. The process of claim 1 wherein the molar ratio of base to alkynol is 1:2.8.

6. The process according to claim 3 wherein the base is added to the reaction mixture over a period of approximately 30 to 60 minutes to maintain the reaction mixture below 20° C.

7. The process according to claim 1 wherein the alkali metal iodide is a potassium iodide.

8. The process of claim 1 wherein the molar ratio of alkali metal halide to alkynol is 1:1.

9. The process according to claim 7 wherein the alkali metal iodide is added to the reaction mixture over a period of approximately 2 to 15 minutes to maintain the reaction mixture below 7° C.

10. The process according to claim 1 wherein the oxidizing agent is dichlorodimethylhydantoin.

11. The process according to claim 1 wherein the oxidizing agent is bromochlorodimethylhydantoin.

12. The process of claim 1 wherein the molar ratio of oxidizing agent to alkynol is 1:2.

13. The process according to claim 1 wherein the oxidizing agent is added to the reaction mixture over a period of approximately 15 minutes to 2 hours to maintain the reaction temperature at approximately 2° C. to 11° C.

* * * * *